United States Patent [19]
Budny et al.

[11] Patent Number: 6,159,447
[45] Date of Patent: *Dec. 12, 2000

[54] COMPOSITIONS FOR CONTROLLING BACTERIAL COLONIZATION

[75] Inventors: John A. Budny; Matthew J. Budny, both of Westlake Village, Calif.

[73] Assignee: PharmaCal Biotechnologies, LLC, Westlake Village, Calif.

[ * ] Notice: This patent is subject to a terminal disclaimer.

[21] Appl. No.: 09/249,674

[22] Filed: Feb. 12, 1999

Related U.S. Application Data

[63] Continuation-in-part of application No. 08/951,393, Oct. 16, 1997, Pat. No. 5,871,714.

[51] Int. Cl.[7] .............................. A61K 7/16; A61K 7/28; A61K 38/00; A61K 31/70
[52] U.S. Cl. .................................. 424/49; 424/50; 514/2; 514/23
[58] Field of Search ........................... 424/49, 50; 514/2, 514/23

[56] References Cited

U.S. PATENT DOCUMENTS

| | | | |
|---|---|---|---|
| 5,202,113 | 4/1993 | London | 424/54 |
| 5,362,480 | 11/1994 | Au et al. | 424/54 |
| 5,871,714 | 2/1999 | Budny | 424/49 |

*Primary Examiner*—Kevin E. Weddington
*Attorney, Agent, or Firm*—Colin P. Abrahams

[57] ABSTRACT

A composition for controlling bacterial growth/colonization is provided. The composition comprises a selected enzyme, a selected anchor molecule coupled to the enzyme to form an enzyme-anchor complex, with the anchor being capable of attaching to a substrate proximal to a bacterial colony. The attachment to the substrate permits prolonged retention time of the enzyme-anchor complex where the bacterial colony is present to increase the effectiveness of the complex. The invention is also for a method of controlling colonization of bacterial plaque in the oral cavity, as well as a method of forming a composition for controlling the proliferation of bacterial colonies in the oral cavity.

47 Claims, 1 Drawing Sheet

COMPOSITIONS FOR CONTROLLING BACTERIAL COLONIZATION

CROSS REFERENCE TO RELATED APPLICATIONS

This application is a continuation-in-part of U.S. application Ser. No. 08/951,393 filed Oct. 16, 1997, issued as U.S. Pat. No. 5,871,714 on Feb. 16, 1999. U.S. Ser. No. 08/951,393 is incorporated herein by reference in its entirety.

FIELD OF THE INVENTION

The invention relates to compositions for controlling bacterial colonization, particularly, but not restricted to, an oral application for reducing dental plaque. The invention is also for an oral therapeutic treatment which will limit or restrict the extent of bacterial colonization in the oral cavity thus reducing the quantity of dental plaque. By controlling the extent or size of plaque structures with enzymes, bacterial colony proliferation and their invasion into gingival tissue can be limited. The invention also relates to methods of manufacturing such compositions.

BACKGROUND OF THE INVENTION

Periodontal disease is one of the oldest and most common diseases of man. It is apparent in human fossil remains and occurs in otherwise healthy individuals. Today, periodontal disease represents a major worldwide health problem. The disease is a result of the accumulation of dental plaque at the gingival margin. There are two broad classes of periodontal disease which roughly approximates the degree or severity of the pathology: gingivitis and periodontitis.

Gingivitis is an inflammation of the marginal gingival tissue due to the accumulation of dental plaque. For the most part, gingivitis is characterized by redness, swelling and bleeding of the gingival tissue. The extent and severity of these characteristics indicate the degree to which the disease has progressed. Periodontitis is characterized not only by the inflammation of the marginal gingivae, but also by loss of the attachment of the periodontal ligament, loss of alveolar bone and loss of the epithelial attachment due to apical migration. The pathological consequences of these physiological losses is the formation of a periodontal pocket, which can become infected, and thus be the source of bacterial infiltration into the host. The progression of established gingivitis to an advanced lesion may well lay the foundation for periodontitis.

The literature indicates that there are significant microbial population shifts from sites of gingival inflammations to subgingival pockets. Certain identified and specific bacterial organisms are known to be responsible for periodontal disease in humans; however, other organisms may also contribute to the severity of the disease. In addition, results from clinical studies show a correlation between the presence of certain microbial species and different types and degrees of severity of periodontal disease. There is a cause-and-effect relationship between the presence and quantity of plaque, containing a wide variety of colonized bacterial strains, and periodontal disease. It therefore follows that, by limiting plaque, the extent and severity of periodontal disease can be controlled.

Both chronic gingivitis and chronic periodontitis share two important characteristics which may be the clue to their sequential relationship. Both conditions are usually painless until their more advanced stages and both pathologies have an absolute requirement for bacterial plaque before the sequence of these conditions progress and develop into advanced periodontal disease. While there are secondary systemic and external factors which affect the extent the disease, the most important factor, and one that provides the greatest promise of being controllable, is the relationship between bacterial plaque and periodontal disease.

The disease begins its progression through an accumulation of bacterial plaque at the gingival margin. As the pathology progresses, there is chronic inflammation of the gingiva and periodontal ligament, with subsequent degeneration of various gingiva-tooth structures. The chronic inflammation is exacerbated by calculus formed from mineralized plaque at the various tissue interfaces and in the periodontal pocket. Epithelial tissue migration into inflamed and necrotic areas can engulf plaque structures, resulting in abscesses accompanied by purulent exudate. The final and most severe stage of periodontal disease is the resorption of alveolar bone and the eventual exfoliation of the tooth.

Plaque is a heterogeneous mixture of bacterial aggregations embedded in a sticky matrix. While bacterial composition of plaque ranges from 50 to 70 percent, the matrix is derived from dead cells, salivary glycoproteins and serum proteins that are laid on a polysaccharide backbone. The bacteria synthesize the polysaccharides for the plaque backbone as a step in their own colonization process. In addition to the viable bacteria and the matrix, plaque also contains food debris, small numbers of epithelial cells, white blood cells and various other components which are derived from the host and the host's activities.

The formation and development or proliferation of plaque occurs in two stages. The first step may require a base layer of salivary glycoproteins on the tooth's surface as well as on the soft tissue in the oral cavity. This base organic layer, derived from saliva, is adsorbed onto the surface and forms an acquired pellicle. This insoluble acquired pellicle serves as the foundation for supragingival plaque. The second step is the bacterial colonization by "pioneering" bacteria of the acquired pellicle. Once the bacteria have attached to the surface of a structure, they aggregate, develop colonies and plague begins to form.

There are well over 100 different bacterial species in various dental plaques. This variation in the types of bacteria is influenced by diet, salivary components and bacterial interactions, to name a few. The location of the plaque in the oral cavity, the time of the day, age of the patient and the status of the general oral hygiene of the patient all contribute to the implications and consequences of dental plaque and periodontal disease. Consequently, it is not surprising that plaque is a heterogeneous collection of bacterial communities attached to the tooth providing a vast array of biochemical and physiological consequences. Two major pathological conditions as consequences are periodontal disease and dental caries.

Enzymes as therapeutic agents present unique possibilities. However, some of the early oral pathology research using enzymes was based on the assumption that they would be bactericidal to colonies of organisms found in plaque and therefore would act as "disinfectants". This approach, however, was not fruitful. Recently, it was shown that treatment of buccal epithelial cells with protease altered bacterial adhesion; however, this treatment also distorted the ratios of various bacterial populations. More promising results were obtained when the focus was shifted from bactericidal action to altering plaque formation. These latter results were seen in vitro and in vivo as well as in animal models and humans in clinical trials. However, these approaches also fell short of desired therapeutic effectiveness most likely because the required time for an effective action exceeded the retention time of the enzyme in the oral cavity. In short, salivary flow, other fluid and food movement and normal mechanical agitation in the oral cavity reduced the retention time of the enzyme(s). These factors shortened the residence time of the enzymes, resulting in less than desirable clinical efficacy.

When enzymes were tested in vitro, the importance of residence time within the oral cavity was not identified as an important issue. There is no indication that the design of these in vitro studies even identified this important variable. These in vitro systems, that demonstrated activity of enzymes in reducing plaque, did, however, identify other important factors. These other factors included: (1) possibly more than one enzyme may be necessary; (2) greater specific activity of the enzyme may be required; (3) a more appropriate enzyme may be required; or (4) a combination of enzymes may be more effective.

Plaque itself is an extremely complex mixture of various components, namely, macromolecules, living and dead cells (whole bacteria and sloughed epithelial cells from the host), cell fragments and various other contributions of material from both the host and the bacterial flora. The pioneering work on the chemical aspects of plaque focused on the carbohydrate or polysaccharide (PS) backbone of plaque. This was an ideal place to start because the PS backbone not only served as a structural element for the plaque matrix, but it also served as a carbohydrate food-store for the growing colonies of bacteria. Most of the research on PS was centered around determining the properties and structure of glucans; however, there are many other components that form the composition of plaque. In reviewing the scientific literature describing previous dental therapeutic research involving enzymes, certain patterns emerge. Most of the enzyme research to control plaque was conducted under the aegis of caries prevention; however, it is well established that plaque control is a fundamental issue related to both caries prevention and the prevention of periodontal disease. The types of investigations carried out included in vitro examination of bactericidal effects, animal studies and clinical investigations involving human experimentation. Furthermore, most of the clinical studies used a mouthwash as the vehicle to deliver the enzymes, while fewer studies used chewing gum.

U.S. Pat. No. 4,138,476 (Simonson) teaches of plaque dispersing enzymes as oral therapeutic agents by molecular alteration. A glucanohydrolase is combined with a phosphate carrier group such that the enzyme itself has increased affinity for the surfaces of the teeth. The modified glucanohydrolase enzyme covalently crosslinks with the carrier, in the presence of a reacting agent such as ethyl chloroformate, and has an increased binding capacity to hydroxyapatite components of the teeth.

U.S. Pat. No. 5,490,988 (Beggs) relates to the delivery of therapeutic agents to a target site. The patent teaches a highly specific process whereby an antibody fragment is able to bind to a target site through antigen-antibody binding, and provides for a therapeutic agent to be connected onto the antibody fragment through an additional peptide appended to the antibody fragment. The product is thus constituted by the antibody fragment, the peptide and the agent.

Examination of the published clinical protocols for evaluating enzymes shows that there were two reasons why the selected enzymes did not completely exert their desired effects, even though limited clinical efficacy was seen:

a. the enzymes were not modified so that they would be held in the oral cavity for an extended period of time; and b. the oral rinsing was done for various durations and various selected times during the day without particular attention to dosing just prior to a time of limited oral activity (swallowing, chewing and saliva generation, etc.) like sleeping.

SUMMARY OF THE INVENTION

A principal aspect of the invention lies in two concepts, both of which are necessary for a successful therapy for the prevention of periodontal disease. The first of these is the regulation of the amount and architecture of the plaque structure within the oral cavity by using enzymes; the second is the means of retaining the enzymes in the oral cavity. Both of these concepts must preferably be implemented for effective control of periodontal disease to occur.

In one aspect, the present invention modifies selected enzymes in a manner that they will have the capability of limiting plaque or its components. The enzymes selected are preferably ones that specifically degrade polysaccharides. In this way, the backbone structure of the plaque matrix may be limited without either selective or broad-spectrum kill of bacteria, thus avoiding any bacterial imbalances.

The invention provides for the selective control of proliferative bacterial colonization and is, therefore, aimed at prevention rather than treatment. The invention is not dependent upon bactericidal activity in the oral cavity which eliminates (a) potential imbalances in normal bacterial populations e.g., overgrowth either in the oral cavity or at other, remote locations in or on the host; (b) the requirement for considering systemic responses of the host which can be either immunologic and toxic; and (c) the need for delivering the active agents below the gingival margin. The emphasis is thus on bacterial adhesion, specifically in the oral cavity.

The modified enzyme is preferably attached to a selected "anchor" molecule(s) to be retained in the oral cavity. The retention of the enzymes in the oral cavity is preferably maximized by coupling the enzymes to specific molecules that will adhere to the structures and existing biofilms within the oral cavity. Enzymatic activity should be maintained after the coupling. It is important that the process of connecting the selected enzymes to the specific anchor molecules does not wholly destroy the enzymatic activity, although it is possible that such activity may be reduced by reason of the coupling. However, at least a minimum effective amount of enzymatic activity should be present after coupling.

In another aspect, the invention also provides a method to determine the extent to which the selected and modified enzymes inhibit oral bacterial plaque growth in an in vitro test system, and in vivo. The selected enzymes which maintain this enzymatic activity after being coupled or derivatized to anchor molecules are suitable for use to inhibit plaque growth.

The product of the invention may, but need not necessarily, take the form of an oral rinse which may be used at bed-time. The modified enzymes in the oral rinse are preferably retained in the oral cavity during a time when salivary and mechanical agitation is low. In addition, the length of retention time (six to eight hours during sleeping) may provide an extended period for the therapeutic enzymes to carry out their desired biochemical reactions.

This invention addresses the paradox with respect to dental plaque: on the one hand, pathogenic factors such as bacteria and plaque are retained in the oral cavity, but, on the other hand, it is difficult to retain potentially therapeutic agents, such as enzymes, in the oral cavity. This paradox may be used to advantage for controlling dental plaque by giving selected enzymes the specific trait that the bacteria use to cause periodontal disease i.e., the ability to adhere to surfaces in the oral cavity. In this invention, significant consideration has been given to the important and necessary idea of increasing retention time in the oral cavity of the antiplaque composition, since it is only by extending the retained time of the composition in the oral cavity that it has the ability to effectively prevent plaque buildup. Where antiplaque compositions spend only a very short duration of time in the oral cavity, their effect is by definition very limiting. For achieving bacterial kill, a short retention time may be adequate; however, with the novel concept of altering and limiting the structural architecture of the bacterial colony growth support media, a longer retention time may be required.

Previous research to reduce or eliminate periodontal disease has, for the most part, been aimed directly at eliminating the bacteria; only little research has been directed at controlling the bacterial environment. The present invention attempts to control bacterial colony growth while at the same time maintaining a balance among the various strains of bacteria in the oral cavity. By controlling the quantity of plaque and limiting the amount of extracellular polysaccharide backbone, the size of the bacterial colonies can be controlled. This control can be achieved through the enzymatic compositions and processes of the invention.

DETAILED DESCRIPTION OF THE PREFERRED EMBODIMENTS

Figure 1:
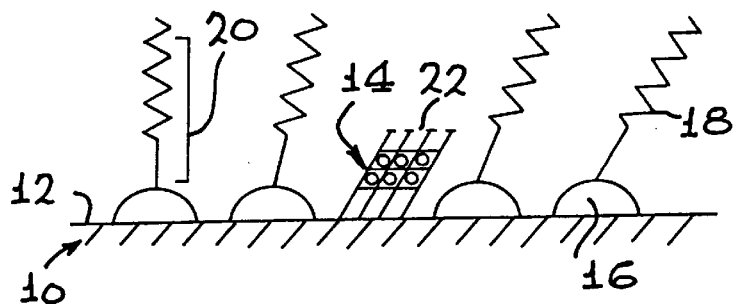
FIG. 1 is a schematic view of the enzyme-anchor complex of the invention, when attached to a tooth.

The present invention proposes to retain selected enzymes in the oral cavity. Unlike incorporating free and nascent enzymes in a dentifrice or oral rinse (where the effects are only transient), enzymes are allowed to have a prolonged opportunity to carry out their desired biochemical reactions and beneficial effects by modifying them so that they can be retained within the oral cavity. In addition, the specific enzymes are preferably selected to minimize toxic responses in the bacteria so as to maintain the normal bacterial balance and at the same time not adversely affect other necessary and protective biofilms, for example, the "acquired pellicle".

Certain polysaccharide degrading enzymes are modified so that they are able to adsorb to surfaces and structures in the oral cavity, and inhibit the proliferative bacterial colonization associated with the plaque matrix. The enzymes are derivatized or coupled to anchor molecules. The anchor portion of the enzyme-anchor complex can then adhere to structures in the oral cavity, inhibiting the buildup of plaque.

*Streptococcus mutans* and plaque are recognized as being intimately involved in the formation of dental caries. This cariogenic bacterium utilizes sucrose to produce substrates for metabolism for the entire microbial population in the oral cavity. The end products of this sucrose-supported metabolism are organic acids which initiate the sequence of steps involved in the formation of dental caries. In addition, *Streptococcus mutans* also uses sucrose to enhance colonization of the oral flora by using the sucrose-supported substrate pool to produce polysaccharides that are complex and water insoluble. This scenario most likely takes place with many other bacteria that are colonized with the dental plaque.

The insoluble polysaccharide structures provide the backbone for extended bacterial colonization which, when aggregated, is the observable film recognized as plaque. While polysaccharides are not a requirement for initial attachment of the "pioneering" bacteria to the tooth's surface, the colonization and perpetuation of colonies requires these insoluble polysaccharides. It is likely that complex polysaccharides, by their insoluble nature, not only cause colonization and proliferation of the initial bacteria, but may also shield the bacteria from therapeutic agents. Consequently, this invention may be used in conjunction with agents that result in bacterial kill, either specific or non-specific. Restricting and controlling the amount of insoluble polysaccharides, and ultimately bacterial colonization into plaque, has a beneficial effect for the prevention and progression of periodontal disease. One of these complex, insoluble polysaccharides is glucan. The enzymatic degradation of glucan is therefore one of the objects of this invention.

The invention provides for a composition and method to immobilize certain glucan degrading enzymes to surfaces and structures in the oral cavity. This inhibits the buildup of plaque which is a necessary precursor step to periodontal disease. Inhibiting proliferative bacterial colonization may well avoid any distortion of the microbial ecology or balance among the various bacterial strains. In general, avoiding bacterial population shifts is desirable because of the potential for over-growth of opportunistic bacteria, some of which may be pathogenic. The composition of the invention seeks to retain the normal relative ratios of the various bacterial strains in the oral cavity. However, the absolute numbers of at least certain strains of the bacteria will be reduced because the colonies thereof will be smaller.

The development of a mechanism to increase the enzyme's residence time in the oral cavity provides the opportunity for increased clinical efficacy. To achieve this goal, effective enzymes must remain in the oral cavity longer to accomplish their intended action. The increased retention time of the enzymes in the oral cavity will control plaque by limiting the polysaccharide backbone of the plaque matrix.

The composition of the invention is thus designed to facilitate a longer residence time for the enzymes in the oral cavity. This approach involves derivatizing, or coupling, the appropriate enzymes with an anchor molecule which will bind to structures in the oral cavity with the anchor portion of the derivatized enzyme-anchor complex. The anchor molecule will be specifically chosen to bind to, for example, existing plaque or the acquired pellicle that covers the tooth. Due to the relatively rapid turnover of epithelial tissue, the mucosal tissue layer within the oral cavity is a less preferred choice of a binding site than either the existing plaque or pellicle.

In one embodiment, two enzymes with the type of enzymatic activity that has been shown to be effective in controlling the carbohydrate structural backbone of plaque are connected to three "anchor" molecules. The six resulting enzyme-anchor complexes are tested in an in vitro test system containing saliva (normal bacteria and host glycoproteins) to assess their ability to control plaque and limit its proliferation by binding to the plaque and causing hydrolytic cleavage of the polysaccharide backbone of the plaque. These enzyme-anchor complexes are assessed for clinical efficacy and optimized, as necessary.

Figure 2:
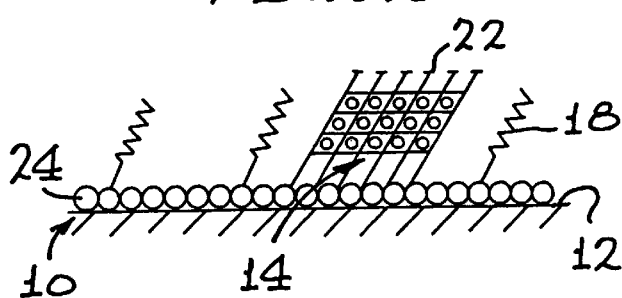
FIG. 2 is a schematic view of the enzyme-anchor complex of the invention, when attached to a pellicle or other surface in the oral cavity.

Reference is made to FIGS. 1 and 2 of the drawings, which schematically illustrate the anchor-enzyme complex of the invention. The drawings are diagrammatic representations, are not intended to be to scale, and are for illustrative purposes only. In FIG. 1, there is shown a tooth 10 having a surface 12. On the surface 12, a colony 14 of bacteria within a matrix is attached to the tooth 10. Also attached on the surface 12 of the tooth is an anchor molecule 16, which may be an adhesion peptide. An immobilized enzyme 18 is attached to the anchor molecule 16, and the anchor molecule 16 and immobilized enzyme 18 together form the anchor-enzyme complex 20. The anchor-enzyme complex 20 competes with the colony 14 for attachment to the surface 12 of the tooth 10 and thus reduces the potential substrate sites for colony 14 attachment. Additionally, and most importantly, the enzyme 18 exercises its catalytic effect on the colony 14, degrading the plaque matrix and/or polysaccharide backbone. In FIG. 1, the termination 22 of the matrix by the enzyme 18 can be seen. The colony 14 will thus be severely impaired in its ability to expand. Furthermore, the anchor-enzyme complex 20 has significant retention time on the tooth surface 12, thus providing more than a temporary obstacle to plaque matrix and colony 14 proliferation.

Another embodiment of the invention is shown in FIG. 2. In this figure, elements corresponding to those in FIG. 1 have been accorded the same reference numeral. In the embodiment shown in FIG. 2, the tooth surface 12 has thereon a pellicle 24 to which the enzyme attaches. The pellicle, which includes peptides, proteins and the like, may provide or constitute the anchor, or a separate anchor molecule preattached to the enzyme may be used.

Figure 4:
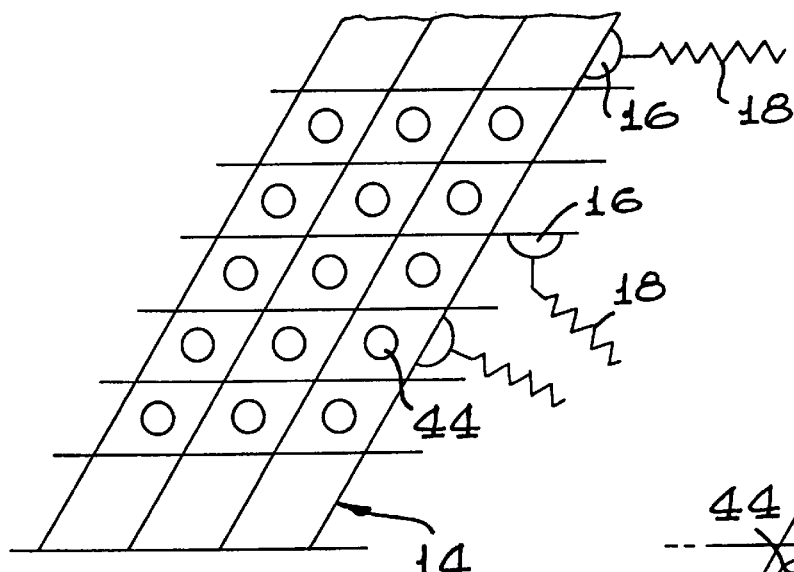
FIG. 4 is a schematic view of the enzyme-anchor complex of the invention, when attached to a bacterial colony matrix in the oral cavity.
Figure 5:
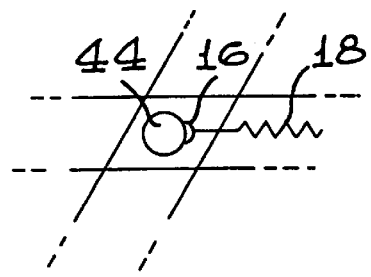
FIG. 5 is a schematic view of the enzyme-anchor complex of the invention, when attached to a bacterium in the bacterial colony matrix in the oral cavity.

In FIG. 4, a detail of a bacterial colony matrix 14 is shown, including individual bacteria 44. In this embodiment, the anchor molecule 16 of the complex 20 attaches to the bacterial matrix, and the termination 22 of the matrix can be clearly seen. In FIG. 5, the anchor 16 of the complex 20 attaches directly on to a bacterium 44 within the matrix 14.

It is within the scope of this invention to expand the enzyme-anchor complex to incorporate polysaccharide-degrading enzymes other than those which hydrolyze or degrade glucans e.g., enzymes that degrade fructose-based polysaccharide, enzymes that hydrolyze glycoproteins etc. The complex could also extend to cover ligand-based anchor molecules that mimic exterior cell surfaces of bacteria so as to create direct competitive binding between bacteria and anchor enzyme complexes. Further, the complex may include receptor-based anchor molecules that mimic the bacterial attachment sites so that anchored enzymes can be adsorbed onto bacterial surfaces that are already adhering to plaque. Finally, anchor molecules comprised of polypeptides that are known adhesion molecules may be used.

Purification of potentially suitable hydrolytic enzymes (polysaccharide hydrolases, glycoprotein degrading enzymes, etc.) may be carried out to achieve higher specific activity and a more focused specific type of reaction.

Thereafter, procedures for determining the extent or degree of coupling between the enzyme and anchor molecules may also be carried out, thus establishing the number of anchor molecules attached to the enzyme that will provide the best combination of enzymatic activity and degree of binding.

It will be appreciated that any effective enzyme which prevents or reduces bacterial colonization may be used in this invention. Preferably, a group of enzymes which have a hydrolytic action, or hydrolases, are used since they are particularly effective. This group facilitates the hydrolysis of chemical bonds that link moieties, which after the hydrolysis reaction occurs, can exist as separate chemical entities. Preferred enzymes which may be used in this invention may be selected from one or more of the following: esterases—those enzymes that cleave ester bonds; glycolytic cleavage enzymes—those enzymes that cleave bonds that are found in oligo- and polysaccharides; ether bond cleavage enzymes; peptide bond cleaving enzymes where proteins are the substrate (reactant); carbon-nitrogen bond cleavage where the substrate (reactant) is not a protein; acid anhydride cleaving enzymes; carbon-carbon bond cleavage; halide bond cleavage; phosphorus-nitrogen bond cleavage; sulfur-nitrogen bond cleavage; and carbon-phosphorus bond cleavage.

The following examples are other enzymes which may be used within the scope of the invention:

A. A combination of purified enzymes or an ersatz mixture of proteases, lipases and/or glycohydrolases in various ratios coupled to one or more various anchors for the ultimate beneficial effect of restricting and/or reducing plaque.

B. Biologic extracts which may be selected from the group consisting of dehydrated pancreas (Viokase) and combinations of trypsin, chymotrypsin, carboxypeptidase, amylase, lipase, nuclease, and fungal and bacterial extracts containing hydrolytic enzymes.

C. Oxidoreductase enzymes, for example, glucose oxidase for the purpose of generating hydrogen peroxide and lactoperoxide-hypothiocyanate. One significant purpose of such enzymes is to degrade and clear debris from the basic polysaccharide backbone structure of plaque.

D. Specific polysaccharide enzymes selected from the group consisting of dextranase, mutanase, mucinase, amylase, fructanase (levanase), galactosidase, glucosidase and glucan hydrolases.

E. Neutral, alkaline and acid proteases.

F. Carbonic anhydrases and other metalloenzymes, lysozymes, muramidases, lactoferrin, kallidrein and other serine proteases for the degrading an clearing of debris from the basic polysaccharide backbone structure of plaque.

It will be appreciated that an enzyme-anchor complex of the invention may incorporate more than one enzyme or class of enzymes. Based on the knowledge that different enzymes or classes thereof may have a different action or effect within the oral cavity in reducing or eliminating plaque, the complex can be constructed such that the anchor, or an intermediate organic molecule of the type discussed below, has attached thereto two or more enzymes selected for their ability to degrade a polysaccharide backbone, for example, at varying stages of formation or at different locations on the backbone. Different enzymes may also be selected and used in a single complex to address the spectrum of bacterial flora typically found in the oral cavity and which may contribute to plaque. The anchor may therefore comprise multiple binding or attachment sites, or an intermediate organic molecule or spacer may have a plurality of functionalities, each of which may be formed to bind to a target enzyme which carries out a specific function in degrading or limiting the plaque.

Anchor molecules and structures for anchoring the enzymes in the oral cavity may be selected from a number of different categories, as set out below:

A. Proteins, protein fragments and polypeptides
   a. naturally-occurring
   b. naturally-occurring, but modified
   c. synthetic polypeptides
      i. using naturally occurring amino acids
      ii. using synthetic, non-naturally occurring amino acids e.g. D-amino acids, β-substituted amino acids, alpha, alpha-disubstituted etc.
   d. charge prevalence
      i. cationic (basic amino acids)
      ii. anionic (acidic amino acids)
      iii. neutral (aliphatic amino acids)
   e. any combination of the above B. saccharides and oligosaccharides
   a. naturally occurring e.g. glucose, mannose, galactose, rhamnose, fucose, fructose, sucrose etc.
   b. naturally occurring amino sugars e.g. glucosamine, galactosamine, N-actylglucosamine, N-acetylgalactosamine, neuramenic acid, sialic acid, etc.
   c. synthetic or non-naturally occurring saccharides and amino sugars
      i. esters of sugars e.g. sugar-organic acid esters etc.
      ii. chemically combined sugars and proteins/polypeptides e.g. synthetic glycoproteins C. Glycoproteins/proteoglycans
   a. naturally occurring e.g. elastin, lectins etc.
   b. synthetic e.g. modified naturally occurring glycoproteins/proteoglycans D. Glycolipids
   a. naturally occurring e.g. sphingomyelin, cerebroside, gangliosides etc.
   b. synthetic e.g. modified natural glycol; lipids through some chemical procedure such as esterification, amidation or similar chemical process E. Lipoprotein e.g. chylomicron, Very Low Density Lipoproteins (VLDL), Low Density Lipoproteins (LDL), High Density Lipoproteins (HDL), etc.

F. Lipids
   a. non-polar, natural or synthetic e.g. triglycerides, cholesterol or other plant or animal sterols, etc
   b. polar, natural or synthetic e.g. phospholipids (phosphatidyl serine), lipoteichoic acid, etc.

G. Cell fragments and cell ghosts—segments or portions of exterior bacterial or animal cell walls or membranes that would mimic live and viable bacterial or animal cells for the purpose of securing an enzyme to the surface within the oral cavity.

H. Non-biologic, polymeric materials
   a. homopolymers e.g. polyethylene glycol (PEG), etc.
   b. copolymers e.g. styrene-butadiene polymers etc.

The anchor may also comprise several other types and classes of compounds, as set forth below.

I. The anchor may include materials that are antigenic to substances and surfaces in the oral cavity. These substances and surfaces may comprise: saliva; salivary components; pellicle coating the teeth and/or prostheses temporarily or permanently located in the oral cavity; cellular components which are either human, bacterial or both; and glycoproteins, glycolipids, proteoglycans and related molecules which may contain a sialic acid moiety as part of their constitution. The salivary components referred to above may include mucopolysaccharides, mucins, glycoproteins, secretary immunoglobulin A, agglutinins, proline-rich proteins (PRPs), histatins, statherin, cystatins, amylases, salivary peroxidases, carbonic anhydrases, lactoferrin, lysozyme, muramidase, kallikrein, fibronectin, and the like.

As an example of how such antigenic materials may be applied, antibodies to saliva may be used as the anchor. In this case, the extracted saliva may be injected into a rabbit resulting in the production of antibodies which are then coupled to an enzyme to form the enzyme-anchor complex. Alternatively, such antibodies can be produced using monoclonal antibody techniques. Such anchors could be highly specific and may be customized for a particular application to provide maximum effect for a particular subject. The anchor would have antigenic activity and display properties associated with the immune response.

J. Bioadhesive molecules may be used as anchors. Polypeptides that fulfill the following criteria may be selected:
   i. rich in basic amino acids, for example, lysine;
   ii. hydroxylated amino acids, whether naturally occurring or synthetic;
   iii. DOPA (D or L-3,4-dihydroxyphenyl alanine);
   iv. copolymers of basic amino acids, DOPA, tyrosine and glutamic acid;
   v. substances which contain any of the following amino acids which constitute di-, tri-, tetra-, penta-, hexa-, hepta-, octa-, nona- and deca-peptides in any arrangement, combination or sequence: proline, lysine, serine, tyrosine, threonine and alanine.

The bioadhesive molecules referred to above may be naturally occurring, synthetic or semi-synthetic, or contain components that are naturally occurring, whether synthetic or semi-synthetic.

K. Polyhydroxide compounds may be employed as anchors, and may include polyphenols, either as singular molecular units or as polymers made up of polyhydroxy or polyphenolic monomeric units. Either the monomeric units or the polymers can be of natural or synthetic origin.

L. The anchor may comprise cross-linked polymers of the type described in J. and K. above.

M. The anchor may also be selected from natural, synthetic or semi-synthetic components of saliva and dental pellicles. This may include: mucopolysaccharides and mucopolysaccharide fragments; mucins, glycoproteins, histatins, statherin, cystatins, amylases, salivary peroxidases, carbonic anhydrases, lactoferrin, lactoperoxidase, lysozyme, muramidase, kallikrein, fibronectin, and the like, as well as their appropriate fragments.

The saliva and pellicle anchors described in this item are to be distinguished from the antigenic materials to substances in the oral cavity described above in item I. There is no overlap. In this example, the anchors are not the antibodies, as is the case in item I. above. In the present example, saliva or its components are used to adhere to the hydroxyapatite of the tooth or other surfaces, whereas in item I. above, the anchor is intended to adhere to coverings on the tooth or other surfaces, such as salivary coatings.

One advantage of using the anchor described in this example is that it can be applied in the oral cavity immediately after a dental tooth and/or mouth cleaning to create an early barrier or impediment to early colonization of bacteria and the initial proliferation of a new or young plaque structure so that later-stage colonization by non-pioneering bacteria is restricted. By having an anchor adhere to the tooth itself soon after a dental cleaning, an immediate and direct antiplaque layer is formed. Thereafter, other types of anchors (which adhere to other types of surfaces) in the enzyme-anchor complex may be used when the actual tooth surface or large portions thereof may no longer be as accessible to such anchors; subsequent anchors in the enzyme-anchor complex may therefore be selected for their ability to adhere to, for example, saliva or other surfaces in the oral cavity.

N. The anchor may comprise or include an organic bifunctional or multifunctional molecule. Preferably, at least one functionality of the organic molecule is capable of binding to an enzyme, and one of its other functionalities possesses the ability to maintain an ionic or charged character. The organic molecule may be natural, synthetic or semi-synthetic. It is preferably non-reactive, or at least is not adverse to the functions and properties of the anchor and enzyme.

In one form, an enzyme-anchor complex comprising or including the at least bifunctional organic molecule may have the formula:

$$F_z\text{-R-}F_{eb}$$

where R is the organic moiety. R may be aliphatic, aromatic, cyclic, heterocyclic, polynuclear aromatic, polymeric (homo- or hetero-monomeric) etc. $F_z$ is the charged (either positive or negative) functionality and may be selected from: carboxylate ($R\text{-}CO_2^-$); sulfonic ($R\text{-}SO_3^-$); sulfate ($R\text{-}OSO_3^-$); phosphonic ($R\text{-}PO_3^-$); phosphate ($R\text{-}OPO_3^-$); phosphinic ($R_{1,2}\text{-}PO_2^-$, where $R_1$ and $R_2$ may be identical or dissimilar); any positive species selected from the group including $(R_x)_4N+$, ammonium salt $R_4P+$, phosphonium salt dipolar functionality including phosphine oxides, phosphoranes, N-oxides, nitro, and others, where there is a charge distribution between the hetero atom and oxygen. Further, $F_z$, while initially possessing an ionic functionality, can be converted to a reactive species, such as a sulfonic acid function conversion to sulfonyl halide, so that the initial $F_z\text{-R-}F_{eb}$ complex is converted to $F_{zx}\text{-R-}F_{eb}$, where X is the halide atom and the $F_{zx}$ portion can be secured to a surface or entity within the oral cavity represented by the formula:

$$\text{SURFACE-}F_z\text{-R-}F_{eb}$$

in which process the halide X is released. Preferably, a covalent bond is formed with existing structure within the oral cavity.

In the formula above, $F_{eb}$ is the enzyme-binding functionality which attaches to the selected enzyme portion of the enzyme-anchor complex, and which is described in further detail elsewhere in this specification.

Some of the advantages of an intermediate organic molecule, which may serve as a spacer molecule between the anchor and enzyme. include:

(a) its role in eliminating or reducing steric hindrance by the plaque structure with the functional capability of the enzyme:

(b) its ability to provide increased mobility of the enzyme while at the same time tethering the enzyme so that it is not lost to the environment; and (c) its ability to allow retention of the enzyme while at the same time allowing the enzyme three-dimensional movement within a confined or restricted space.

In one embodiment, one functionality of the organic molecule attaches to an enzyme, another functionality attaches to an anchor, while the organic radical is located therebetween, and may constitute a spacer in the enzyme-anchor complex, providing additional length and structure. The additional length of the complex molecule may serve to enhance the enzymatic characteristics of the enzyme portion of the complex, making the complex more effective as an antiplaque agent. This enhanced activity of the enzyme may be result of the enzyme simply being spatially distanced from the surface on which the complex is attached or located, i.e. a physical advantage, or it may be as a result of an absence of or reduction in steric hindrance between the enzyme and other components including the anchor. In either case mentioned above, the organic molecule may therefore preferably be selected for its properties so as to permit the enzyme to degrade the plaque matrix optimally in the circumstances.

Another potential advantage of incorporating the intermediate organic molecule is that situations may exist where it is desirable or necessary to introduce the complex into the oral cavity in stages. In other words, the anchor molecule may be introduced into the oral cavity as a first step to bind on a desired surface or substance within the oral cavity, and the enzyme introduced thereafter to bind to the anchor. In this procedure, the derivatization between anchor and enzyme to form the complex occurs in the oral cavity and not in vitro. The derivatization within the oral cavity would also be desirable where, for example, the enzyme tends to become removed or separated from the anchor over a period of time due to the degradation of the bond between them, or due to other factors. In such a case, if the anchor continues to be attached at the desired sites within the oral cavity, the complex could be formed once more by simply introducing the enzyme into the oral cavity, and allowing it to complex with the existing anchor. The presence of an organic molecule may assist in the reattachment of enzymes to the in situ anchor molecules to form the complex.

O. The anchor component may comprise a non-dialyzable material obtained from cranberry juice.

P. The anchor may be an adhesin receptor polysaccharide comprised of repeating units of hexa-saccharide that contains a glycerol moiety linked through a phosphodiester bond to the C6 atom of one of the saccharide units in the hexa-saccharide, specifically the α-galactopyranosyl residue. The individual saccharide resides in the hexa-saccharides are connected end to end with the following structure:

Glyc(1→PO$_4$→6)→[→3)Rhapα(1→2)Rhapα(1→3)Galpα(1→3)Galpβ(1→4)Glcpβ(1→3)Galfβ(1→]$_n$.

The hexa-saccharide unit is connected end to end with identical hexa-saccharide units through the galactofuranosyl-β(1→3)-rhamnopyranosyl linkage.

Likewise, serving also as an anchor, is the complement adhesin to the above receptor polysaccharide which is a 155 kDa protein. The protein exists on the exterior surface of bacterial cell walls just as the receptor polysaccharide. In its normal functioning, the 155 kDa protein serves as a ligand and the polysaccharide structure as the receptor.

In addition, glucan dependent aggregation may be mediated by bacterial lectins which serve the purpose of permitting bacteria to adhere to saccharide and polysaccharide surfaces. Many streptococci strains produce glucan-binding lectins (GBLs) or glucan-binding proteins (GBPs). Many of these bacterial strains produce glucosyltransferases that contain glucan-binding domains (GBDs). Such lectins, glucosyltransferases and segments of the glucosyltransferase enzyme that contain GBDs can also serve as anchors within the context of the invention.

The connections between the anchor molecules and the enzymes may also take a number of forms. These connections may thus be chemical, chemisorption, or covalent bonds, including: amide (peptide); ester; glycosidic (sugar linkages); and/or ether. The connections may also be physical, physisorption such as: van der Waals attractive forces, including lipophilicity; charge-charge attractions/interactions, including electrostatic interactions; and/or hydrogen bonding, including hydrophilicity.

Figure 3:
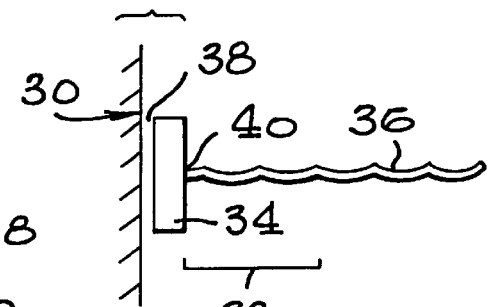
FIG. 3 is a schematic view of a further embodiment of the enzyme-anchor complex of the invention, when attached in the oral cavity.

The connections between the anchor of the anchor-enzyme complex and the surface substrate within the oral cavity would typically be the same as those listed in the preceding paragraph. With reference to FIG. 3 of the drawings, there is shown in schematic form a substrate 30 which is a surface in the oral cavity such as a tooth, existing plaque, an appliance or mucosal tissue, and an anchor-enzyme complex 32 attached thereto. The anchor-enzyme complex 32 comprises an anchor portion 34 and an enzyme portion 36. There is an anchor-surface interface 38 between the complex 32 and the substrate 30 and an anchor-enzyme connection 40. It is believed that there will be a greater tendency for the connection between the enzyme portion 36 and the anchor portion 34 to be of the chemical type, while the interaction between the anchor portion 34 of the anchor-enzyme complex 32 and the substrate 30 is more likely to be of the physical type.

It is apparent that the anchor of the complex "carries" the enzyme to the site of action and "holds" the enzyme at this site to perform its intended function. It follows that there are two necessary contact points or areas of interaction: first, the anchor with the enzyme; and second, the anchor with the substrate or surface in the oral cavity. These components may interact with each other in two general ways, namely, a bonded interaction and a non-bonded interaction. A bonded interaction requires a covalent bond. The contact is firm, strong and not susceptible to any easy disassociation. This type of interaction is an atom-to-atom bonding and is without a continuing or ongoing kinetic element. A non-bonded interaction may also be strong but is however amenable to the laws governing association/disassociation and equilibrium relationships such as association constants, partition coefficients etc. This type of interaction is non-chemical bonding and has a continuing kinetic element for the duration of the interaction.

The interactions between components in this invention may be of either the bonded or non-bonded type. Examples of the bonded type of interaction include covalent bonds of carbon-to-carbon, carbon-to-nitrogen, sulfur-to-sulfur, etc. These interactions would also be referred to as cross-linking, ester or ether, peptide or amide and disulfide formations. Non-bonded types of interactions would include those such as hydrophobic, ionic (charge-charge interactions), receptor-ligand interactions, hydrogen bonding, van der Waals attractive forces, etc.

While in its simplest form, the invention has at least two points of contact (anchor to enzyme and anchor to substrate), there can be other contact points if the system is more complicated. For example, there can be enzyme-to-enzyme and anchor-to-anchor contact for complexes having multiple enzymes and anchors respectively.

Some of the different types of specific interactions are summarized below:

(a) anchor to enzyme contact in a bonded fashion;

(b) anchor to enzyme contact in a non-bonded fashion;

(c) anchor to surface contact in a bonded fashion;

(d) anchor to surface contact in a non-bonded fashion;

(e) anchor to anchor contact in a bonded fashion;

(f) anchor to anchor contact in a non-bonded fashion;

(g) enzyme to enzyme contact in a bonded fashion; and (h) enzyme to enzyme contact in a non-bonded fashion.

There will be a greater tendency for the connection between the enzyme and anchor to be of the chemical type. The interaction of the anchor portion of the anchor-enzyme complex will more likely be of the physical type.

As already alluded to above, the enzyme-anchor complex or composition may consist of various combinations of anchors and enzymes that are connected to form a complex such that the individual and independent actions work together for the ultimate beneficial effect of restricting, limiting and/or reducing plaque structures.

One composition may consist of a complex of the formula $F_z$-R-$F_{eb}$ and various combinations of complimentary inorganic anions, such as phosphate, sulfate, nitrate, chloride and the like, when the $F_z$-R-$F_{eb}$ complex is cationic in character. When the $F_z$-R-$F_{eb}$ complex is anionic in character, the inorganic ions are cationic in character, for example, calcium and all other metals in Group IA and IIA of the Periodic Table.

An anchor-enzyme complex may consist of multiple anchors and/or multiple enzymes. The multiplicity of enzymes in a single complex has already been mentioned above, and offers advantages in reducing, preventing or eliminating plaque at various stages of its formation. Further, several types of enzymes may attack different structures and forms of polysaccharide backbones as well as the wide range of bacteria which aggregate to create the complex plaque structures. The complex may also have more than one type of anchor, allowing the complex to attach for prolonged retention in various environments within the oral cavity. Thus, a complex may have some anchor molecules which bind to the teeth, others which bind to pellicles, coatings or other surfaces in the oral cavity, and yet others which have the ability to attach to bacterial cell surfaces. The diversity of an anchor-enzyme complex with two or more anchors and/or enzymes therefore has the affect of increasing and extending its action to all areas in the oral cavity.

Example

An embodiment of the invention involves selection of two enzymes known to have activity on degrading the polysaccharide backbone of the dental plaque matrix. Two such enzymes are:

1) α-Glucosidase EC 3.2.1.20; [(1→3) 3-glucanohydrolase]. α-Glucosidase is commercially available. While the enzyme shows greatest activity toward α-1,4 glucose linkage, it will also hydrolyze α-1,2 and α-1,3 linkages. The enzyme will also hydrolyze α-1,6 linkages, but only at a very slow rate.

2) Dextranase EC 3.2.1.11; [(1→6)6-glucanohydrolase]. Dextranase is also commercially available. This enzyme cleaves glucose molecules from polysaccharides that are linked α-1,6.

Many researchers describe the glucan structure as α-1→3 and α-1→6. Glucan has also been described as having α-1→4 and α-1→2 linkages. From a structural perspective, α-1→6 linkages give the glucan its length and the α-1→3, α-1→4, and α-1→2 linkages gives the glucan its branching characteristics. It is not known whether glucan length or glucan branching is important for bacterial colonization. For this reason, the two commercially available enzymes were selected: α-Glucosidase, providing cleavage activity for α-1→4, α-1→2 and α-1→3 i.e., cleaving at branching points in the glucan structure; and Dextranase, which will provide cleavage of α-1→6 linkage i.e., cleavage at lengthening linkages.

These enzymes will be separately coupled with each of the following "anchor" molecules:

1) a basic polypeptide e.g., Lys-Lys-Glu-Lys-Lys or some similar basic polypeptide;
2) an acidic polypetide e.g., Glu-Glu-Lys-Glu-Glu or some similar acidic polypeptide.

Teichoic acids and lipoteichoic are important bacterial cell wall components for binding. These components are also associated with phosphate esters which would present an anionic character to the exterior portion of the bacterial cell surface. For this reason, the anchor molecule, Lys-Lys-Glu-Lys-Lys, which is a cationic species, would be attracted to the bacterial cell wall.

Since available evidence suggests that the bacterial cell surface is anionic in character, it is reasonable to suspect the colonization of bacteria on to portions of plaque that are principally cationic in character. Indeed, if there are regions or areas of cationic character associated with plaque, the anchor molecule, Glu-Glu-Lys-Glu-Glu, which is an anionic species that would be attracted to the cationic regions of plaque, would be a good choice.

Additionally, or alternately, any other densely arranged lipid character such as micelles may serve as either a substrate in the oral cavity or the anchor molecule to which the enzyme-anchor complex attaches.

The rationale of charge attractions, as the basis for anchoring selected enzymes to various organic structures in the oral cavity, may be one factor for bacterial attachment. However, bacterial adhesion in the colonization of plaque also may involve factors other than charge attraction alone. Thus, specific proteins may be responsible for the binding of oral bacteria to polysaccharide (glucan) and plaque. However, the actual mechanism for bacterial binding in plaque does not preclude other binding mechanisms for enzymes that are connected to specific anchor molecules, and would be encompassed by this invention.

The enzymes and anchors set out in this example will produce six derivatized enzymes with the potential for a broad charge-binding capability.

Synthesis

The synthesis part of the derivatized enzyme-anchor complexes involves coupling of each anchor molecule to the two individual enzymes. The basic polypeptide Lys-Lys-Glu-Lys-Lys is coupled to the two enzymes through the free carboxyl group of the Glu residue and there is some coupling through the "C" terminus of the polypeptide. The acidic polypeptide Glu-Glu-Lys-Glu-Glu is coupled through the free amino group of the Lys residue and there is some coupling through the "N" terminus of the polypeptide to the two enzymes.

Purification of the six derivatized enzyme reaction products may be carried out by molecular size exclusion on column chromatography. The purified coupled enzymes may be assayed and compared to the underivatized enzymes to determine any changes in enzymatic activity as a consequence of the coupling procedure.

The six anchor-enzyme complexes produced in this example, or complexes of other enzymes and anchors, may further be tested in the in vitro system prior to clinical application. Any suitable procedure for testing may be used, for example, the procedure of Drake [Drake, D. R., Vargas, K., Cardenzana, A. and Srikantha, R. "Enhanced bactericidal activity of Arm and Hammer dental care." *Am. J. Dent.* 8, 308–312(1995)] or a modification thereof.

The basic and acidic polypeptides, which are commercially available, for example from Peptides International, Louisville, Ky., are synthesized, for example, by a variation of the solid-phase method. These starting materials may be used without purification; however, a retained portion of each starting material should preferably be assayed for purity, as necessary e.g., to describe unexpected reaction products, etc.

The enzymes, which are also commercially available and may be purchased from United States Biochemical, Cleveland, Ohio and Worthington Biochemical, Freehold, NJ, may also be used without purification. Other enzymes which can be used and which may not be commercially available can be isolated and purified from tissues and organisms, using standard procedures. A retained portion of each enzyme, too, should be analyzed, only if necessary to determine purity. Such purification analyses may be important depending upon the results of the in vitro experimentation. These analyses may be conducted using the retained portions of the enzymes.

The enzymatic activity should preferably be determined both before and after the derivatization (coupling) reaction and this can readily be accomplished using, for example, 4-nitrophenyl-α-D-glucose in a standard assay procedure.

The basic polypeptide, Lys-Lys-Glu-Lys-Lys may be coupled to each of the enzymes using a modification of the procedure described by Williams (1981). [Williams, A. and Ibrahim, I. A. "A mechanism involving cyclic tautomers for the reaction with nucleophiles of the water-soluble peptide coupling reagent 1-ethyl-3-[-3-dimethylaminopropyl]-carbodiimide (EDC)." *J. Am. Chem. Soc.* 103, 7090–7095 (1981)]. This procedure uses 1-ethyl-3-[-3-dimethylaminopropyl]-carbodiimide (EDC) as the coupling agent. The EDC-activated carboxyl group of Glu in the polypeptide (as well as the carboxyl group from the "C" terminus end of the polypeptide) will be coupled to free amine groups on the enzymes, forming covalent amide bonds.

The acidic polypeptide, Glu-Glu-Lys-Glu-Glu, may be coupled to each of the enzymes using a modification of the procedure described by O'Shannessy (1987). [O'Shannessy, D. J. and Hofmann, W. L. "Coupling antibodies for site directed immobilization." Biotech. *Appl. Biochem.* 9, 488–496(1987)]. In this procedure, the free amine group of Lys (as well as the free amine group from the "N" terminus of the polypeptide) is converted to an aldehyde and then coupled to the free amine groups on the enzymes.

In both of the coupling or derivatization reactions involving the polypeptide anchor molecules, there will be a wide variety of byproducts produced; however, there will also be a wide diversity among the sizes of the molecules (molecular weights) which will allow a cleanup procedure using, for example, HPLC with a 3000 Pw column for a separation based on molecular size.

The purpose of this separation step is a "cleanup" of the reaction. The clean-up removes unreacted polypeptide anchor molecules, polypeptide mixtures resulting from the anchor molecules that reacted with each other, and the desired product of enzyme-anchor complexes. There may also be a number of desired enzyme-anchor complexes, depending upon the number of anchor molecules attached to the enzyme. It is not considered necessary to separate enzyme-anchor complexes into discrete fractions depending upon the number of anchor molecules; rather, all types of enzyme-anchor complexes may be tested and clinically applied collectively. Separating the types of enzyme-anchor complexes into discrete molecular entities may, however, be carried out where it is considered appropriate.

Where desired or considered necessary, the clean up procedure may be validated by defining and setting the column (HPLC) operating conditions. Sample runs may be made with: 1) the enzyme alone; 2) the anchor molecule alone; and 3) the reaction mixture without the addition of enzyme. Retention time/fraction number for total protein will be determined under the defined operating conditions that will allow separation of free anchor molecules, reaction products among anchor molecules, free enzyme and derivatized or coupled enzymes.

In Vitro Assay

Prior to clinical application, the effectiveness of any synthesized enzyme-anchor complexes may be determined in an in vitro assay. One such assay is described below.

Subjects are screened for salivary output and a high level of *Streptococcus mutans* and *Actinomyces viscosus* (plate counts) which are recognized as high plaque-forming bacteria. Salivary output from the selected population may be stimulated by chewing an inert material such as parafilm or carbowax. The collected saliva will serve as the stock inoculum solution. This stock solution will be prepared by combining the saliva samples with the greatest population of the identified stains (20–25% of the total samples taken).

Thereafter, the following solutions are prepared:
a) Enriched Sucrose Broth.
b) Positive control solution of 20 mg/ml of chlorohexidine, a known inhibitor of plaque formation.
c) The two test related controls may be the underivatized enzyme i.e., enzymes without anchor molecules.
d) The 8 treatment solutions (6 test solution and 2 test related controls) may be prepared with Enriched Sucrose Broth as the solvent, giving stock solutions with concentrations of 10, 1.0, and 0.1 mg/ml.

Procedure

Sterile glass slides are placed in 50 ml test tubes containing 39 ml of Enriched Sucrose Broth. The tubes are inoculated with 1 ml of stock inoculum (saliva) solution. The tubes are incubated at 37° C. under 5% $CO_2$ for 24 to 48 hours, until visual evidence of plaque formation appears. The slides are removed, transferred to dosing solutions of fresh Enriched Sucrose Broth (39 ml in 50 ml test tubes) to which 1 ml of the appropriate test solution is added. The dosing solutions may have the following composition:

1) No treatment control—Enriched Sucrose broth
2) Positive control—20 mg/ml chlorohexidine
3) Control related to treatments 1A, 1B and 1C—1.0 mg/ml unanchored α-Glucosidase
4) Control related to treatments 2A, 2B and 2C—1.0 mg/ml unanchored Dextranase
5) Test treatments 2A, 2B and 2C (3 Dextranase-anchor): 10, 1.0 and 0.1 mg/ml.
6) Test treatments 2A, 2B and 2C (3 Dextranase-anchor): 10, 1.0 and 0.1 mg/ml.

The glass slides remain in their respective dosing solutions for approximately one hour. They are then removed and rinsed by dipping in a clean Enriched Sucrose Broth.

The slides may then be placed in fresh Enriched Sucrose Broth and the tubes incubated in the same manner for 24 to 48 hours. The amount of plaque is recorded (photographed) for each treatment and the plaque from each slide is harvested, dried and weighed.

The enzymatic activity of both enzymes before and after the derivatization is determined, as well as the efficiency of the reaction cleanup. Visual observation is made of each test; photographs are taken of each treatment (combined triplicate test of each treatment as a single photograph), and the amount (weight) of plaque formed in each test is determined.

In the selection of enzymes, anchors and the coupling methods and procedures, a number of factors should be taken into account to provide the most effective enzyme-anchor complexes. Some of these are as follows: The enzymes and anchor molecules selected should always be the most appropriate for limiting a bacterial colonization matrix. More than one enzyme may be necessary to cause a critical limitation of the polysaccharide backbone for plaque formation.

The potential advantages of this invention are threefold: 1) it does not require bactericidal activity, 2) normal microbial balance in the oral cavity will be maintained, and 3) the likelihood of adverse effects in the host at sites removed from the oral cavity are minimized or eliminated.

What is claimed is:

1. A composition for controlling bacterial growth/colonization in the oral cavity comprising:
   an enzyme,
   an anchor molecule coupled to the enzyme to form an enzyme-anchor complex, the anchor being capable of attaching to a substrate proximal to a bacterial colony, the anchor being selected from group consisting of: materials antigenic to substances or surfaces in the oral cavity, bioadhesive molecules, polyhydroxide compounds, salivary components, and oral cavity pellicle components;
   wherein the attachment to the substrate permits prolonged retention time of the enzyme-anchor complex where the bacterial colony is present.

2. A composition as claimed in claim 1 wherein the materials antigenic to substances or surfaces in the oral cavity are derived from one or more of the group consisting of: saliva; salivary components; pellicle coating in the oral cavity; cellular components; and glycoproteins, glycolipids, proteoglycans and related molecules that contain a sialic acid moiety as part of their constitution.

3. A composition as claimed in claim 2 wherein the salivary components are selected from the group consisting of mucopolysaccharides, mucins, glycoproteins, secretary immunoglobulin A, agglutinins, proline-rich proteins (PRPs), histatins, statherin, cystatins, amylases, salivary peroxidases, carbonic anhydrases, lactoferrin, lactoperoxidase, lysozyme, muramidase, kallikrein, and fibronectin.

4. A composition as claimed in 1 wherein the bioadhesive molecules comprise polypeptides having components selected from at least one of the following:
   i. rich in basic amino acids;
   ii. hydroxylated amino acids;
   iii. DOPA (D or L-3,4-dihydroxyphenyl alanine);
   iv. copolymers of basic amino acids, DOPA, tyrosine and glutamic acid;
   v. substances which contain any of the following amino acids which constitute di-, tri-, tetra-, penta-, hexa-, hepta-, octa-, nona- and deca-peptides in any arrangement, combination or sequence: proline, lysine, serine, tyrosine, threonine and alanine; and vi. proline-rich proteins (PRPs).

5. A composition as claimed in claim 1 wherein the polyhydroxide compounds comprise one or more of molecular units of polyphenols, and polyphenol polymers made up of polyhydroxy or polyphenolic monomeric units.

6. A composition as claimed in claim 1 wherein the salivary components and dental pellicles are selected from the group consisting of mucopolysaccharides and mucopolysaccharide fragments, mucins, glycoproteins, histatins, statherin, cystatins, amylases, salivary peroxidases, carbonic anhydrases, lactoferrin, lactoperoxidase, lysozyme, muramidase, kallikrein, fibronectin, and fragments thereof.

7. A composition as claimed in claim 1 wherein the interaction between the anchor and the substrate and the anchor and the enzyme is a bonded interaction.

8. A composition as claimed in claim 7 wherein the bonded interaction is selected from one or more of: covalent bonds of carbon-to-carbon, carbon-to-nitrogen, sulfur-to-sulfur, cross-linking bonds, ester, ether, peptide, amide and disulfide bonds.

9. A composition as claimed in claim 1 wherein the interaction between the anchor and the substrate and the anchor and the enzyme is a non-bonded interaction.

10. A composition as claimed in claim 9 wherein the non-bonded interaction is selected from the following interactions: hydrophobic, ionic (charge-charge interactions), receptor-ligand interactions, hydrogen bonding, van der Waals attractive forces.

11. A composition as claimed in claim 1 wherein the enzyme is selected for its ability to degrade a colonization matrix.

12. A composition as claimed in claim 11 wherein the colonization matrix includes polysaccharides, and the enzyme is selected for its ability to degrade the polysaccharides.

13. A composition as claimed in claim 1 wherein the anchor molecule is capable of attaching to any suitable substrate within an oral cavity.

14. A composition as claimed in claim 13 wherein the anchor molecule attaches to a tooth surface.

15. A composition as claimed in claim 13 wherein the anchor attaches to a pellicle on a tooth surface.

16. A composition as claimed in claim 13 wherein the anchor molecule attaches to a bacterial cell wall.

17. A composition as claimed in claim 13 wherein the surface in the oral cavity is a plaque matrix.

18. A composition as claimed in claim 12 wherein the polysaccharide is glucan.

19. A composition as claimed in claim 12 wherein the polysaccharide is a heterogenous and complex aggregate and mixture of many diverse oligo- and polysaccharides.

20. A composition for controlling bacterial growth/colonization in the oral cavity comprising:

an enzyme, an anchor molecule attachable to the enzyme to form an enzyme-anchor complex, the anchor being capable of attaching to a substrate proximal to a bacterial colony, an organic molecule having at least two functionalities for binding to the enzyme and the anchor respectively, and wherein the attachment to the substrate permits prolonged retention time of the enzyme-anchor complex where the bacterial colony is present.

21. A composition as claimed in claim 20 wherein the organic molecule is represented by the formula:

$$F_z\text{-R-}F_{eb}$$

wherein $F_z$ is a charged functionality binding to the anchor, R is an organic moiety and $F_{eb}$ is the enzyme binding functionality.

22. A composition as claimed in claim 21 wherein the organic molecule is a spacer between the anchor and the enzyme.

23. A composition as claimed in claim 21 wherein the charged functionality $F_z$ is selected from the group consisting of carboxylate ($R\text{-}CO_2^-$); sulfonic ($R\text{-}SO_3^-$); sulfate ($R\text{-}OSO_3^-$); phosphonic ($R\text{-}PO_3^-$); phosphate ($R\text{-}OPO_3^-$); phosphinic ($R_{1,2}\text{-}PO_2^-$, where $R_1$ and $R_2$ may be identical or dissimilar); any positive species selected from the group including $(R_x)_4N+$, ammonium salt $R_4P+$, phosphonium salt dipolar functionality including phosphine oxides, phosphoranes, N-oxides, nitro, where there is a charge distribution between the hetero atom and oxygen.

24. A composition as claimed in claim 21 wherein R is has one or more of following structures: aliphatic, aromatic, cyclic, heterocyclic, polynuclear aromatic, polymeric (homo- or hetero-monomeric).

25. A composition as claimed in claim 21 wherein $F_z$ initially possesses an ionic functionality convertible to a reactive species, so that the initial $F_z\text{-R-}F_{eb}$ complex is converted to $F_{zx}\text{-R-}F_{eb}$, where X is a halide atom and the $F_{zx}$ portion can be secured to a surface or entity within the oral cavity represented by the formula:

$$\text{SURFACE-}F_z\text{-R-}F_{eb}$$

wherein the halide X is released.

26. A composition as claimed in claim 25 wherein a sulfonic acid converts to sulfonyl halide.

27. A composition as claimed in claim 20 wherein the organic molecule has multiple functionalities whereby two or more anchors may be attached thereto.

28. A composition as claimed in claim 20 wherein the organic molecule has multiple functionalities whereby two or more enzymes may be attached thereto.

29. A composition for controlling bacterial growth/colonization in the oral cavity comprising:

an enzyme selected from the group consisting of a combination of purified enzymes or an ersatz mixture of proteases, lipases and/or glycohydrolases in various ratios;

an anchor molecule coupled to the enzyme to form an enzyme-anchor complex, the anchor being capable of attaching to a substrate proximal to a bacterial colony;

wherein the attachment to the substrate permits prolonged retention time of the enzyme-anchor complex where the bacterial colony is present.

30. A composition for controlling bacterial growth/colonization in the oral cavity comprising:

an enzyme selected from the group consisting of biologic extracts, oxidoreductase enzymes, polysaccharide-degrading enzymes, proteases, carbonic anhydrases, and a mixture of any two or more thereof;

an anchor molecule coupled to the enzyme to form an enzyme-anchor complex, the anchor being capable of attaching to a substrate proximal to a bacterial colony;

wherein the attachment to the substrate permits prolonged retention time of the enzyme-anchor complex where the bacterial colony is present.

31. A composition as claimed in claim 30 wherein the biologic extracts are selected from the group consisting of: dehydrated pancreas (Viokase) and combinations of trypsin, chymotrypsin, carboxypeptidase, amylase, lipase, nuclease, and fungal and bacterial extracts containing hydrolytic enzymes.

32. A composition as claimed in claim 30 wherein the oxidoreductase is glucose oxidase.

33. A composition as claimed in claim 30 wherein the polysaccharide-degrading enzyme is selected from the group consisting of dextranase, mutanase, mucinase, amylase, fructanase (levanase), galactosidase, glucosidase and glucan hydrolases.

34. A composition as claimed in claim 30 wherein the protease is neutral, alkaline or acid proteases.

35. A composition as claimed in claim 30 wherein the carbonic anhydrases are selected from one or more of metalloenzymes, lysozymes, muramidases, lactoferrin, kallidrein and other serine proteases for the degrading and clearing of debris from the basic polysaccharide backbone structure of plaque.

36. A method of controlling bacterial colonization comprising the steps of:
    forming an anchor-enzyme complex comprised of an enzyme selected for its ability to degrade at least portion of a colonization matrix, and an anchor, a portion of which is coupled to the enzyme to produce the complex; and
    selecting the anchor based on the ability of said anchor to attach to a substrate, to thereby increase the retention time of the enzyme-anchor complex in close proximity to the matrix.

37. A method of forming a composition for controlling the proliferation of bacterial colonies, the method comprising:
    selecting an enzyme based on its ability to degrade the structural component where bacterial colonization occurs;
    selecting an anchor molecule based on its ability to couple to the selected enzyme such that the enzyme retains effective enzymatic activity to degrade the structural component, the anchor molecule further being selected for its ability to attach to a substrate proximal the bacterial colonization; and
    coupling the anchor and enzyme to produce an enzyme-anchor complex.

38. A method as claimed in claim 37 for controlling proliferation of bacterial colonies in the oral cavity.

39. A method of treatment for controlling the proliferation of bacterial colonies, the method comprising:
    selecting an enzyme based on its ability to degrade the structural component where bacterial colonization occurs;
    selecting an anchor molecule based on its ability to couple to the selected enzyme such that the enzyme retains effective enzymatic activity to degrade the structural component, the anchor molecule further being selected for its ability to attach to a substrate proximal the bacterial colonization;
    introducing the anchor molecule in to the oral cavity;
    introducing the enzyme in to the oral cavity; and
    allowing the anchor and enzyme to couple in the oral cavity to produce an enzyme-anchor complex.

40. A method as claimed in claim 39 wherein an intermediate organic molecule having at least two functionalities is attached to the anchor, each functionality binding to an anchor and an enzyme respectively.

41. A composition as claimed in claim 1 wherein the anchor is a non-dialyzable material obtained from cranberry juice.

42. A composition as claimed in claim 1 wherein the anchor is an adhesin receptor structure.

43. A composition as claimed in claim 1 wherein the anchor is an adhesin molecule.

44. A composition as claimed in claim 1 wherein the anchor is a bacterial lectin.

45. A composition as claimed in claim 1 wherein the anchor is selected from a glucan-binding lectin (GBL), a glucan-binding protein (GBP), a glucosyltransferase, and a glucan-binding domain (GBD) of a whole or part of a glucosyltransferase enzyme.

46. A composition as claimed in claim 1 wherein the anchor attaches to lipoteichoic acid.

47. A composition as claimed in claim 1 wherein the anchor is antigenic to lipoteichoic acid.

* * * * *